United States Patent [19]

Rasoul

[11] Patent Number: 4,617,399
[45] Date of Patent: Oct. 14, 1986

[54] 2-AMINOBENZOTHIAZOLE 6-CARBONYL CHLORIDE HYDROCHLORIDE

[75] Inventor: Husam A. A. Rasoul, Racine, Wis.

[73] Assignee: Celanese Corporation, New York, N.Y.

[21] Appl. No.: 718,681

[22] Filed: Apr. 1, 1985

[51] Int. Cl.$^4$ .................. C07D 277/60; C07D 277/62; C08G 69/12
[52] U.S. Cl. .................... 548/152; 528/321; 528/327
[58] Field of Search ................. 548/152; 528/321, 327

[56] References Cited

U.S. PATENT DOCUMENTS 3,260,700  7/1966  Rudner et al. ............ 528/321
3,445,466  5/1969  Hahn et al. ............... 548/152

Primary Examiner—Harold D. Anderson
Attorney, Agent, or Firm—Depaoli & O'Brien

[57] ABSTRACT

This invention provides 2-aminobenzothiazole-6-carbonyl chloride hydrochloride, which can be condensed under polymerization conditions to form a novel benzothiazole-polyamide polymer consisting of a recurring monomeric unit corresponding to the formula:

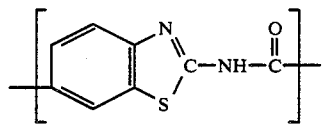

1 Claim, No Drawings

2-AMINOBENZOTHIAZOLE 6-CARBONYL CHLORIDE HYDROCHLORIDE

BACKGROUND OF THE INVENTION

Extensive effort has been directed to the synthesis and characterization of extended chain or rod-like polymers. The unique properties of anisotropic solutions of these polymers has led to the preparation of high modulus/high strength fibers.

The aromatic polyamides are illustrative of this class of rod-like polymers. The liquid crystal behavior is attributable to the linearity of monomer catenation and the predominately trans-configuration of the amide group which is formed during the polycondensation reaction.

There is continuing interest in the development of advanced polyamide compositions which can meet aerospace and other high performance specifications.

Accordingly, it is an object of this invention to provide novel polyamide homopolymers and copolymers which exhibit high temperature stability properties.

It is another object of this invention to provide novel benzothiazole-polyamide polymers which form anisotropic solutions.

It is a further object of this invention to provide a novel benzothiazole-containing monomer for the preparation of liquid crystalline polyamide compositions.

Other objects and advantages of the present invention shall become apparent from the accompanying description and examples.

DESCRIPTION OF THE INVENTION

One or more objects of the present invention are accomplished by the provision of a polyamide which is comprised of a recurring monomeric unit corresponding to the formula:

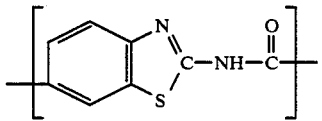

In another embodiment the present invention provides a process for producing a polymer which comprises reacting 2-aminobenzothiazole-6-carbonyl chloride hydrochloride monomer under polymerization conditions to form a benzothiazole-polyamide consisting of a recurring monomer unit corresponding to the formula:

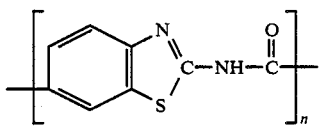

where n is an integer having a value of at least 2.

The process provides a homopolymer product when the 2-aminobenzothiazole-6-carbonyl chloride hydrochloride monomer self-condenses under the polymerization conditions.

If two monomers are utilized in the process, then a copolymeric condensation product is obtained. For example, the condensation of 2-aminobenzothiazole-6-carbonyl chloride hydrochloride with p-aminobenzoyl chloride hydrochloride yields a copolymer which is composed of random monomeric units and/or the following type of recurring comonomeric unit:

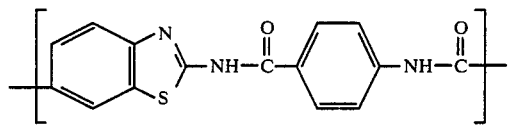

In the practice of the invention polymerization process, typically the monomer starting material is dissolved in a polar solvent, and the reaction medium is stirred and heated in an inert atmosphere for a period sufficient to complete the condensation-polymerization reaction.

The monomer starting material is employed in a quantity between about 10–50 weight percent, based on the weight of solvent.

The polymerization temperature can vary in the range between about 50°–200° C., and preferably is in the range between about 80°–150° C.

The polycondensation reaction period can vary in the range between about 0.5–10 hours, and usually will be in the range between about 1–5 hours.

The pressure employed in the polymerization process can be varied from subatmospheric to superatmospheric, with ambient pressure being the most convenient. The polymerization reaction preferably is conducted under a blanket of an inert gas such as nitrogen, helium or argon.

The polar solvent employed in the polymerization process usually is one that can dissolve the benzothiazole-polyamide product of the process. Illustrative of suitable solvents are conc. sulfuric acid, fuming sulfuric acid, hydrofluoric acid, chlorosulfonic acid, bromosulfonic acid, methanesulfonic acid, chloromethanesulfonic acid, trichloromethanesulfonic acid, trifluoromethanesulfonic acid, N-methylpyrrolidone, hexamethylphosphoramide, dimethylacetamide, tetramethylurea, and the like. The polymer solvating ability of an organic solvent medium can be enhanced by inclusion of a salt such as lithium chloride.

A present invention benzothiazole-polyamide polymer product can be separated and recovered as a precipitate by diluting the polymerization medium with an organic solvent such as methanol or tetrahydrofuran.

Depending on the conditions of the invention polymerization process, polymers are obtained which have an Inherent Viscosity (I.V.) in the range between about 0.1–5.0. The average molecular weight of a benzothiazole-polyamide homopolymer will vary between about 2000–20,000. A polymer molecular weight above about 9000 is preferred for applications involving fibers or films, e.g., a homopolymer containing an average of about 40–100 monomer units.

A lower molecular weight polymer can be obtained by employing a polymerization reaction medium solvent which is a poor solvent or a non-solvent for the benzothiazole-polyamide product as it forms. In this type of polycondensation system, the polymer product precipitates before it attains a high molecular weight.

The invention polymerization process conditions can be selected to provide a final reaction product medium which is a solvent solution of benzothiazole-polyamide polymer. This solvent solution can be employed directly in various application without intervention of a polymer recovery procedure.

In a further embodiment, the present invention provides an anisotropic dope comprising a solvent solution containing a benzothiazole-polyamide which is characterized by a recurring monomeric unit corresponding to the formula:

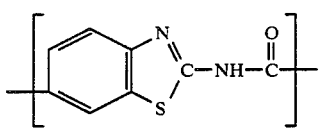

The solvent employed can be dimethylacetamide or any of the other solvent types listed previously hereinabove. The concentration of benzothiazole-polyamide in the anisotropic dope can vary between about 10–30 weight percent, based on the total weight of dope.

The anisotropic dope has good stability, flowability and spinnability, and can be formed into fibers and films having good mechanical properties and thermal stability by extrusion of the doped through a spinning orifice or a slit.

The 2-aminobenzothiazole-6-carbonyl chloride hydrochloride employed as a monomer in the present invention polymerization process is a novel compound. It can be prepared in accordance with the following reaction scheme:

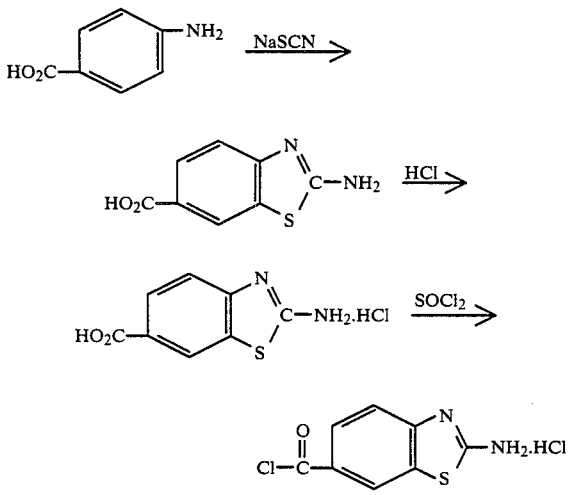

2-Aminobenzothiazole-6-carbonyl chloride hydrochloride is hygroscopic in nature, so that storage of the compound in a moisture-free environment is advantageous.

The following examples are further illustrative of the present invention. The components and specific ingredients are presented as being typical, and various modifications can be derived in view of the foregoing disclosure within the scope of the invention.

EXAMPLE I

This Example illustrates the preparation of 2-amino-6-carboxybenzothiazole hydrochloride.

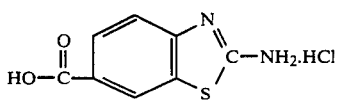

The following synthesis method is similar to that described on page 21 in SRI International Technical Report AFOSR-TR-80-1370 (Dec. 15, 1980) prepared for the Air Force Office Of Scientific Research, Building 410, Bolling AFB, Washington, D.C. 20332.

A 3-necked flask fitted with a mechanical stirrer, thermometer, addition funnel, and argon source is charged with 137 g of 4-aminobenzoic acid (1 mole), 171 g of sodium thiocyanate (2.35 mole) and one liter of methanol. The system is flushed with argon and stirred until the solution is clear.

The reaction medium is cooled to $-5°$ C. with rapid stirring. Under an argon atmosphere and with the temperature maintained at $-5°$ to $-10°$ C., 160 g of bromine (1.05 mole) are added over a two hour period. The reaction mixture is then stirred an additional two hours, during which the temperature is not allowed to rise above $5°$ C.

The product, in the form of a pale yellow precipitate, is collected by filtration, stirred with an equal volume of water, and filtered again. The recovered solid is mixed with one liter of 1N HCl, and the mixture is heated to boiling, filtered, and to the filtered solution is added 0.5l of concentrated HCl. Upon cooling, colorless crystals precipitate from the solution. The crystals are collected and recrystallized using the same procedure, and dried to yield 150 g (65% yield), m.p. 288°–294° C. Mass spectrum ($M^+ = 194$) and infrared analysis confirmed the structure.

EXAMPLE II

This Example illustrates the preparation of 2-aminobenzothiazole-6-carbonyl chloride hydrochloride in accordance with the present invention.

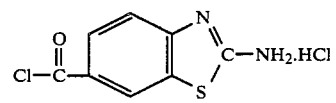

A solution of 69.23 g (0.3 mole) of 2-amino-6-carboxybenzothiazole hydrochloride in 250 g of tetramethylene sulfone is charged to a 3-necked flask fitted with a mechanical stirrer, addition funnel, and argon inlet and outlet. Thionyl chloride (65 ml, 0.83 mole) is added dropwise while the temperature is maintained at 40° C. during the addition and for 24 hours thereafter.

The reaction mixture is cooled to room temperature, and added to 300 ml of dry methylene chloride. The resulting precipitate is filtered, washed with dry methylene chloride and dried in a desiccator to yield 71.4 g (95%) of product. Infrared analysis confirms the structure of the compound. Mass spectrum analysis indicates a molecular weight of 212.

EXAMPLE III

This Example illustrates process embodiments for the polymerization of 2-aminobenzothiazole-6-carbonyl chloride hydrochloride in accordance with the present invention.

A.
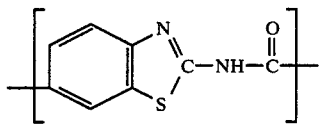

A 3-necked flask fitted with a mechanical stirrer, reflux condenser and argon inlet and outlet is charged with 30 g of 2-aminobenzothiazole-6-carbonyl chloride hydrochloride (0.12 mole) and 270 g of 2% lithium chloride solution in dimethylacetamide.

The reaction medium is stirred at 100° C. for four hours, with the formation of a small quantity of a light yellow precipitate.

The reaction medium is cooled to room temperature, and poured into two liters of methanol to precipitate all of the polymer product. The precipitate is filtered, washed with methanol, and dried to yield 19.3 g (97% of polymeric product with an Inherent Viscosity(I.V.) of 0.11 (1.0% solution in methanesulfonic acid).

Following the general procedure described above, 30 g of 2-aminobenzothiazole-6-carbonyl chloride hydrochloride (0.12 mole) and 490 g of a 4% solution of lithium chloride in N-methylpyrrolidone are charged to the reaction flask. The reaction medium is stirred at 120° C. for four hours, with the formation of a light yellow precipitate.

The reaction medium is cooled to room temperature and the precipitate is separated by filtration. The precipitate is washed with methanol, and dried to yield 16.3 g (81%) of polymer product with an Inherent Viscosity of 0.2 (1.0% solution in methanesulfonic acid).

The reaction medium filtrate is poured into three liters of methanol and the resulting precipitate is filtered, washed with methanol, and dried to yield additional polymer product with an Inherent Viscosity of 0.1.

A polymer prepared in the above described manner is dissolved in methanesulfonic acid to form an anisotropic dope and then extruded through a spinning orifice to form fibers having good mechanical properties and thermal stability.

What is claimed is:

1. 2-Aminobenzothiazole-6-carbonyl chloride hydrochloride corresponding to the structural formula:

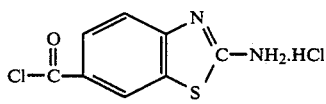

* * * * *